United States Patent
Sookraj et al.

(10) Patent No.: US 10,899,622 B2
(45) Date of Patent: Jan. 26, 2021

(54) BIOBASED CARBON FIBERS AND CARBON BLACK AND METHODS OF MAKING THE SAME

(71) Applicant: Novomer, Inc., Boston, MA (US)

(72) Inventors: Sadesh Sookraj, Boston, MA (US); Herb Munsterman, Boston, MA (US); Han Lee, Chicago, IL (US)

(73) Assignee: Novomer, Inc., Rochester, NY (US)

( * ) Notice: Subject to any disclaimer, the term of this patent is extended or adjusted under 35 U.S.C. 154(b) by 314 days.

(21) Appl. No.: 15/950,850

(22) Filed: Apr. 11, 2018

(65) Prior Publication Data

US 2019/0002293 A1 Jan. 3, 2019

Related U.S. Application Data

(60) Provisional application No. 62/527,340, filed on Jun. 30, 2017, provisional application No. 62/556,355, filed on Sep. 9, 2017.

(51) Int. Cl.

| | | |
|---|---|---|
| *C01B 32/205* | (2017.01) | |
| *D01F 9/22* | (2006.01) | |
| *C01B 32/05* | (2017.01) | |
| *C08F 120/44* | (2006.01) | |
| *C07C 231/10* | (2006.01) | |
| *D01D 5/06* | (2006.01) | |
| *C07C 253/20* | (2006.01) | |
| *C09C 1/44* | (2006.01) | |
| *C09C 1/48* | (2006.01) | |
| *C07C 231/02* | (2006.01) | |
| *C09C 3/12* | (2006.01) | |
| *C09C 1/56* | (2006.01) | |

(52) U.S. Cl.
CPC ............ *C01B 32/205* (2017.08); *C01B 32/05* (2017.08); *C07C 231/02* (2013.01); *C07C 231/10* (2013.01); *C07C 253/20* (2013.01); *C08F 120/44* (2013.01); *C09C 1/44* (2013.01); *C09C 1/48* (2013.01); *D01D 5/06* (2013.01); *D01F 9/225* (2013.01); *C01P 2004/16* (2013.01); *C09C 1/56* (2013.01); *C09C 3/12* (2013.01)

(58) Field of Classification Search
CPC ..... C01B 32/205; C01B 32/05; C07C 231/10; C07C 253/20; C08F 120/44; D01D 5/06; D01F 9/225
See application file for complete search history.

(56) References Cited

U.S. PATENT DOCUMENTS

2017/0247309 A1* 8/2017 Porcelli .................. C07C 51/12

OTHER PUBLICATIONS

Karp, Eric M., et al. "Renewable acrylonitrile production." Science 358.6368 (2017): 1307-1310.*

* cited by examiner

*Primary Examiner* — Richard M Rump
(74) *Attorney, Agent, or Firm* — Young Basile Hanlon & MacFarlane, P.C.

(57) ABSTRACT

Bio-based materials, e.g., epoxide starting material, a beta-lactone starting material and/or a beta-hydroxy amide starting material, may be used as feedstocks in processes for making and using acrylonitrile and acrylonitrile derivatives to produce, among other products, carbon fibers and carbon black.

30 Claims, No Drawings

BIOBASED CARBON FIBERS AND CARBON BLACK AND METHODS OF MAKING THE SAME

This application claims priority to and the benefit of application Ser. No. 62/527,340 filed on Jun. 30, 2017, and application Ser. No. 62/556,355 filed on Sep. 9, 2017, both of which are incorporated herein by reference.

FIELD OF THE INVENTION

The present invention relates generally to the production of biobased carbon fiber and carbon black from biobased acrylonitrile derivatives and a methods thereof. Specifically, the processes of the present invention provide high-purity acrylonitrile and acrylonitrile derivatives through a series of reactions beginning with biobased epoxide and biobased carbon monoxide reagents. The present invention also relates to using the produced acrylonitrile or acrylonitrile derivative for the production of many useful commercial products such as carbon fibers.

BACKGROUND OF THE INVENTION

Acrylonitriles are an important class of compounds that can be used in various industrial applications. For example, acrylonitrile may be used as a starting material in the production of polymers and monomer precursors, i.e. polyacrylonitrile. Acrylonitrile or polyacrylonitrile can also be used to produce commercially useful products such as carbon fiber. Carbon fibers are novel high-performance materials described as fibers containing at least 90% carbon obtained by the controlled pyrolysis of appropriate fibers. Carbon fibers have excellent tensile properties, low densities, high thermal and chemical stabilities in the absence of oxidizing agents, good thermal and electrical conductivities, and excellent creep resistance. In recent years, the carbon fiber industry has been growing steadily to meet the demands arising from different applications such as aerospace (aircraft and space systems), military, turbine blades, construction, lightweight cylinders and pressure vessels, medical, automobile, and sporting goods.

Various methods for the industrial production of acrylonitrile are known in the art. For instance, acrylonitrile is prepared by the catalytic ammoxidation of propylene, in which propylene, ammonia and air are contacted with a catalyst at elevated temperature and pressure. Ammoxidation of alkenes exploits weak covalent bonds located in the allylic position of unsaturated hydrocarbons. Benzylic covalent bonds are also susceptible to ammoxidation.

The term "carbonylation" generally refers to chemical reactions that introduce carbon monoxide molecules into other organic and inorganic substrate molecules. Carbonylation results in a substrate molecule gaining a carbonyl (C=O) functional group. Carbonylation reactions are important in industrial chemistry and are becoming a more important building block for fine and bulk chemicals. Specifically, catalytic carbonylation of cyclic compounds including epoxides, aziridines, thiiranes, oxetanes, lactones, lactams, and analogous compounds is useful for the synthesis of the ring expanded products of such compounds.

Further commercial and industrial benefit results in modifying cyclic compounds through a process known as ring opening polymerization which is a form of chain-growth polymerization. In ring opening polymerization, the terminal end of a polymer chain acts as a reactive center where further cyclic monomers can react by opening cyclic rings and forming a longer polymer chain. Under certain conditions, ring-opening polymerization proceeds via radical, anionic or cationic polymerization. Certain beta-lactones, such as beta-butyrolactone, beta-valerolactone, beta-heptanolactone, beta-tridecanolactone, cis-3,4-dimethyloxetan-2-one, 4-(butoxymethyl)-2-oxetanone, 4-[[[(1,1-dimethylethyl)dimethylsilyl]oxy]methyl]-2-oxetanone, and 4-[(2-propen-1-yloxy)methyl]-2-oxetanone, 4-[(benzoyloxy)methyl]-2-oxetanone, to name a few, undergo ring opening polymerization to produce certain polylactones.

Polylactones such as polypropiolactone, polylactide, polyglycolide, and polycaprolactone are generally biodegradable aliphatic polyesters comprised of bio-based monomers. The polylactones are generally stable, have low toxicity, and are easily transported and stored at remote locations. Recent advances in the carbonylation of epoxides—such as in U.S. Pat. No. 6,852,865—and the ring opening polymerization of beta-propiolactone intermediates has provided more efficient synthetic routes to polylactones. The recent advances in production of polylactones, combined with the physical and chemical properties thereof, make polylactones ideal for many commercial and industrial applications. However, conventional processes are less effective at producing highly pure polylactones. Certain polylactones thermally decompose through a process known as thermolysis.

Generally, thermolysis is a chemical decomposition process in which heat causes the cleavage of one or more covalent bonds. In at least one mechanism for thermolysis of polymers, heat converts a polymer of chain length "n" into a polymer of chain length "n−1" and produces a molecule of vinyl organic acid.

Alternative methods suitable for the industrial production of acrylonitrile and derivatives thereof are desired in the art, including methods of producing such compounds, either in part or completely, from renewable resources.

SUMMARY OF THE INVENTION

An object of the present invention is to provide for the processes which may produce biobased carbon fiber and carbon black from one or more biobased acrylonitrile products such as polyacrylonitrile.

In preferred aspects of the present invention, the and processes of the present invention are customizable and/or configurable for performing a series of chemical reactions such as carbonylation, polymerization, thermolysis, esterification and ammoxidation. In preferred aspects of the present invention, the acrylonitrile products are wholly or partially comprised of reagents from bio-based and/or renewable sources.

In preferred embodiments, the processes of the present invention provide for carbonylation of epoxide reagents with carbon monoxide reagents to produce beta-lactone intermediates which are directly converted to organic acids or undergo ring opening polymerization to produce polylactone products. The processes of the present invention are configured to provide heat for thermolysis to decompose the polylactone products and produce organic acid products. In certain embodiments, the processes are configured for esterification of the organic acid products to produce ester products. The processes may configured for ammoxidation of acrolein and/or the organic acid products and/or the ester products to produce acrylonitrile products. Advantageously, polylactone products are more safely transported from a reactor in one location to a reactor in another, remote location for thermolysis.

In a preferred embodiment, the processes overcome the deficiencies of conventional systems by providing for carbonylation of a broad range of epoxide reagents with carbon monoxide reagents to form a broad range of beta-lactone intermediates. At least a portion of the epoxide reagents and/or carbon monoxide reagents are derived from bio-base and/or renewable sources. Advantageously, the versatile processes of the present invention are configured to provide a broad range of acrylonitrile products to meet demands driven by environmental concerns, regulatory changes, consumer trends, and/or production costs to name a few.

In preferred embodiments of the present invention, the processes comprise the following steps: introducing an epoxide reagent and a carbon monoxide reagent to at least one reaction vessel through at least one feed stream inlet; contacting the epoxide reagent and carbon monoxide reagent with a carbonylation catalyst in the at least one reaction vessel to produce a beta-lactone intermediate; polymerizing the beta-lactone intermediate with an initiator in the presence of a metal cation in the at least one reaction vessel to produce a polylactone product; heating the polylactone product under thermolysis conditions in the at least one reaction vessel to produce an organic acid product; optionally esterifying the organic acid product to produce an ester product; and reacting the organic acid product and/or ester product with an ammonia reagent under ammoxidation conditions to produce an acrylonitrile product. Advantageously, the processes of the present invention may control the presence of contaminates, impurities, catalytic materials, and/or reagents to provide for highly pure acrylonitrile products.

Still another object of the invention is to provide a method of producing acrylonitrile or an acrylonitrile derivative from beta-hydroxy amides and/or beta-lactones. In particular, the invention provides a method of producing a compound of formula (3):

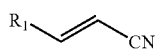
(3)

wherein $R_1$ is H or alkyl,
or isomers thereof, the method comprising:

combining a compound of formula (2) with a dehydration agent to produce the compound of formula (3), or isomers thereof, wherein:

the compound of formula (2) is

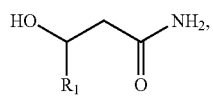
(2)

wherein $R_1$ is as defined above for formula (3), and the dehydration agent comprises phosphorous pentoxide, an organophosphorous compound, a carbodiimide compound, a triazine compound, an organosilicon compound, a transition metal complex, or an aluminum complex, or any combination thereof.

In certain aspects, the method further comprises combining a compound of formula (1) with ammonia to produce the compound of formula (2), wherein:

the compound of formula (1) is

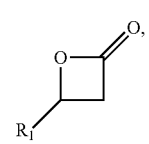
(1)

wherein $R_1$ is as defined above for formula (3).

In another aspect, the invention provides a method of producing a compound of formula (3), wherein formula (3) is as defined above, or isomers thereof, the method comprising: combining a compound of formula (1) with ammonia and a dehydration agent to produce the compound of formula (3), wherein formula (1) is as defined above, and the dehydration agent comprises phosphorous pentoxide, an organophosphorous compound, a carbodiimide compound, a triazine compound, an organosilicon compound, a transition metal complex, an aluminum complex, or any combination thereof.

In yet another aspect, the invention provides a composition comprising a compound of formula (2), wherein formula (2) is as defined above; and a dehydration agent comprising phosphorous pentoxide, an organophosphorous compound, a carbodiimide compound, a triazine compound, an organosilicon compound, a transition metal complex, or an aluminum complex, or any combination thereof.

In still another aspect, the invention provides a composition comprising a compound of formula (3), wherein formula (3) is as defined above, or isomers thereof.

In some variations of the foregoing, the composition further comprises a compound of formula (1), wherein formula (1) is as defined above; and ammonia.

In another aspect, the invention provides a composition comprising a compound of formula (1), wherein formula (1) is as defined above; ammonia; and a dehydration agent comprising phosphorous pentoxide, an organophosphorous compound, a carbodiimide compound, a triazine compound, an organosilicon compound, a transition metal complex, or an aluminum complex, or any combination thereof.

In some variations of the foregoing, the composition further comprises a compound of formula (3), wherein formula (3) is as defined above, and isomers thereof.

In yet another aspect, the acrylonitrile or acrylonitrile derivatives produced by the above methods are used to produce commercial products, such as for example, carbon fibers.

While this disclosure is susceptible to various modifications and alternative forms, specific exemplary embodiments thereof are shown by way of example in the drawings and are herein described in detail. It should be understood, however, that there is no intent to limit the disclosure to the particular embodiments disclosed, but on the contrary, the intention is to cover all modifications, equivalents and alternatives falling within the scope of the disclosure as defined by the appended claims.

DETAILED DESCRIPTION OF EMBODIMENTS

The following description sets forth exemplary processes, parameters and the like. It should be recognized, however, that such description is not intended as a limitation on the scope of the present disclosure but is instead provided as a description of exemplary aspects.

Acrylonitrile Production from Acrylic Acid

In preferred embodiments of the present invention, the processes may produce acrylonitrile products from epoxide reagents, carbon monoxide reagents, and ammonia reagents through a series of reactions. One exemplary embodiment of a series of reactions that produces a highly pure acrylonitrile product is as follows:

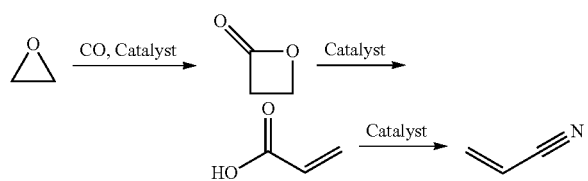

Another exemplary embodiment is as follows:

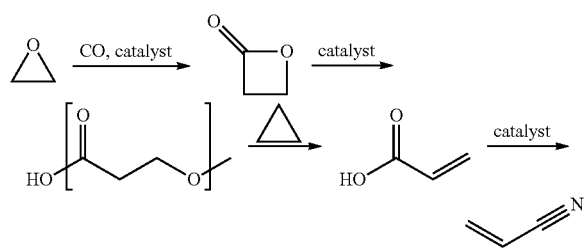

Preferred embodiments of the present invention are directed to producing a biobased acrylonitrile products comprising the following steps: introducing an epoxide reagent and a carbon monoxide reagent to at least one reaction vessel through at least one feed stream inlet; contacting the epoxide reagent and carbon monoxide reagent with a carbonylation catalyst in the at least one reaction vessel to produce a beta-lactone intermediate; polymerizing the beta-lactone intermediate with an initiator in the presence of a metal cation in the at least one reaction vessel to produce a polylactone product; heating the polylactone product under thermolysis conditions in the at least one reaction vessel to produce an organic acid product; and reacting the organic acid product with an ammonia reagent under ammoxidation conditions in the at least one reaction vessel to produce a biobased acrylonitrile product. In certain preferred embodiments, biobased carbon fiber and biobased carbon black are produced by polymerizing the acrylonitrile product to produce a polyacrylonitriole and carbonizing the polyacrylonitrile to produce carbon fiber and carbon black. In certain preferred embodiments, the processes of the present invention is performed in two or more reaction vessels. Advantageously, the processes of the present invention controls the presence of contaminates, impurities, catalytic materials, and/or reagents to provide for highly pure acrylonitrile products. In some embodiments, a step for esterification of the organic acid product is performed prior to ammoxidation. In certain preferred embodiments, the processes of the present invention produce an organic acid product directly from a beta-lactone intermediate.

Carbonylation of Epoxides

In preferred embodiments of the present invention, the processes include a step for introducing an epoxide reagent and carbon monoxide reagent to at least one reaction vessel through at least one feed stream inlet 111. The epoxide reagent and/or carbon reagent enters the at least one reaction vessel with mechanical assistance and/or by natural forces. In some embodiments, a mechanical pump assists in introducing the at least one epoxide reagent and carbon monoxide reagent to the at least one reaction vessel through the at least one feed stream inlet. In some embodiments, epoxide reagent and carbon monoxide reagent are stored at a higher pressure than the at least one reaction vessel so that the epoxide reagent and carbon monoxide reagents enter the at least one reaction vessel by the natural equalizing of pressure.

In certain preferred embodiments, the processes of the present invention include an epoxide reagent and one or more carbon monoxide reagent fed into the at least one reaction vessel at an amount sufficient for carbonylation under superatmospheric pressure. In certain embodiments, the epoxide reagent and carbon monoxide reagent are provided at a pressure in the range from about 50 psi (350 kPa) to about 5000 psi (35 MPa). In certain embodiments, the epoxide reagent and carbon monoxide reagent are provided at a pressure from about 50 psi (350 kPa) to about 1000 psi (7 MPa), at a pressure from about 50 psi (350 kPa) to about 500 psi (3.5 MPa), at a pressure from about 100 psi (700 kPa) to about 400 psi (2.8 MPa), or at a pressure of about 200 psi (1.4 MPa). In certain embodiments, the epoxide reagent and carbon monoxide reagent are provided under an atmosphere having a partial pressure of CO of about 200 psi (1.4 MPa). The super-atmospheric pressure of the carbon monoxide reagent is provided in the form of pure carbon monoxide, or by introducing a gas mixture containing two or more sources of carbon monoxide. In other embodiments, the epoxide reagent and carbon monoxide reagent are provided mixed with one or more inert gases. In certain preferred embodiments, the epoxide reagent and carbon monoxide reagent are comprised of bio-based carbon. Preferably, the biological material used to produce bio-based carbon monoxide is gasified, and the ethylene oxide is derived from corn ethanol. Bio-based ammonia is obtained from many sources such as, for example, food grains such as corn, wheat and rice.

In some embodiments, the processes of the present invention introduce the epoxide reagent and carbon monoxide reagent at least about 1000 kg/hr, at least about 2000 kg/hr, at least about 5000 kg/hr, at least about 10000 kg/hr, or at least about 16000 kg/hr. In some embodiments, the processes of the present invention introduce the epoxide reagent and carbon monoxide reagent at least about 30 kmol/hr, or at least about 60 kg/hr. In some embodiments, the epoxide reagent and carbon monoxide reagent are introduced at about 1000 kg/hr to about 16000 kg/hr, about 2000 kg/hr to about 16000 kg/hr, or about 4000 kg/hr to about 16000 kg/hr. In some embodiments, the processes of the present invention introduce the epoxide reagent and the carbon monoxide reagent at least about 30 kmol/hr or at least about 500 kmol/hr. In some embodiments, the flow rate from the epoxide reagent and/or the carbon monoxide reagent is set to about the stoichiometric value for the carbonylation reaction, to about 5% higher than the stoichiometric value, to about 10% higher than the stoichiometric value, to about 15% higher than the stoichiometric value, or to about 20% higher than the stoichiometric value.

In preferred embodiments, the processes of the present invention include a step for contacting the epoxide reagent and carbon monoxide reagent with a carbonylation catalyst in at least one reaction vessel to produce a beta-lactone intermediate 113. Within the at least one reaction vessel, the epoxide reagent and carbon monoxide reagent contact the carbonylation catalyst to produce a beta-lactone intermediate, as generally depicted in the reaction scheme below:

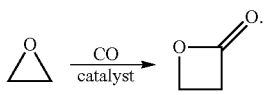

Carbonylation utilizes a metal carbonyl-Lewis acid catalyst such as those described in U.S. Pat. No. 6,852,865. In other aspects, the carbonylation step is performed with one or more of the carbonylation catalysts disclosed in U.S. patent application Ser. Nos. 10/820,958 and 10/586,826. In other aspects, the carbonylation step is performed with one or more of the catalysts disclosed in U.S. Pat. Nos. 5,310, 948; 7,420,064; and 5,359,081. Additional catalysts for the carbonylation of epoxides are discussed in a review in Chem. Commun., 2007, 657-674. The entirety of each of the preceding references is incorporated herein by reference.

Table 1 illustrated below includes Column A directed to a non-exhaustive list of epoxides which may undergo carbonylation to produce beta-lactone intermediates according to the processes of the present invention and Column B directed to a non-exhaustive list of beta-lactone intermediates which may undergo ring opening polymerization to produce polylactones according to the processes of the present invention. It is to be understood that the beta-lactones presented in Column B of Table 1 can be used to produce the corresponding acrylonitrile derivatives through the methods disclosed herein.

TABLE 1

| Column A | Column B |
| --- | --- |
|  |  |
|  | or/and |
|  |  |
|  |  |
|  |  |
|  |  |
|  |  |
|  |  |
|  |  |

TABLE 1-continued

| Column A | Column B |
|---|---|
| (glycidyl acetate) | (β-lactone with CH₂OC(O)CH₃) |
| (allyl glycidyl ether) | (β-lactone with CH₂O-allyl) |
| (isopropyl glycidyl ether) | (β-lactone with CH₂O-iPr) |
| (n-butyl glycidyl ether) | (β-lactone with CH₂O-n-Bu) |
| (benzyl glycidyl ether) | (β-lactone with CH₂OBn) |
| (glycidyl benzoate, Bz) | (β-lactone with CH₂OC(O)Ph) |
| (3,3,3-trifluoropropylene oxide) | (β-lactone with CH₂CF₃) |
| (1,2-epoxybutane) | (β-lactone with Et) |
| (2-(benzyloxy)ethyl oxirane) | (β-lactone with CH₂CH₂OBn) |
| (tetrafluoroethyl glycidyl ether) | (β-lactone with CH₂OCF₂CHF₂) |

TABLE 1-continued

| Column A | Column B |
|---|---|

TABLE 1-continued

| Column A | Column B |
|---|---|
| glycidyl methacrylate (epoxide with methacrylate ester) | β-lactone with methacrylate ester (methacrylate on CH₂ attached to β-lactone) |
| 1,2-epoxy-5-hexene | 4-(but-3-en-1-yl)-β-propiolactone |
| cyclohexyl ethylene oxide | 4-cyclohexyl-β-propiolactone |
| styrene oxide | 3-phenyl-β-propiolactone |
| furfuryl glycidyl ether | 4-((furan-2-ylmethoxy)methyl)-β-propiolactone |
| epoxide with ethyl butanoate linker (n-Pr ester) | β-lactone with ethyl butanoate linker (n-Pr ester) |
| 1,2-epoxy-3-hydroxyoctane (n-C₅H₁₁) | β-lactone with hydroxyl and n-C₅H₁₁ |
| cyclohexylidene epoxide | cyclohexylidene β-lactone |
| benzyl epoxide (2-benzyloxirane) | 4-benzyl-β-propiolactone |
| pentafluorobenzyl epoxide | 4-(pentafluorobenzyl)-β-propiolactone |
| phenyl glycidyl ether | 4-(phenoxymethyl)-β-propiolactone |

TABLE 1-continued

| Column A | Column B |
|---|---|

TABLE 1-continued
| Column A | Column B |
|---|---|
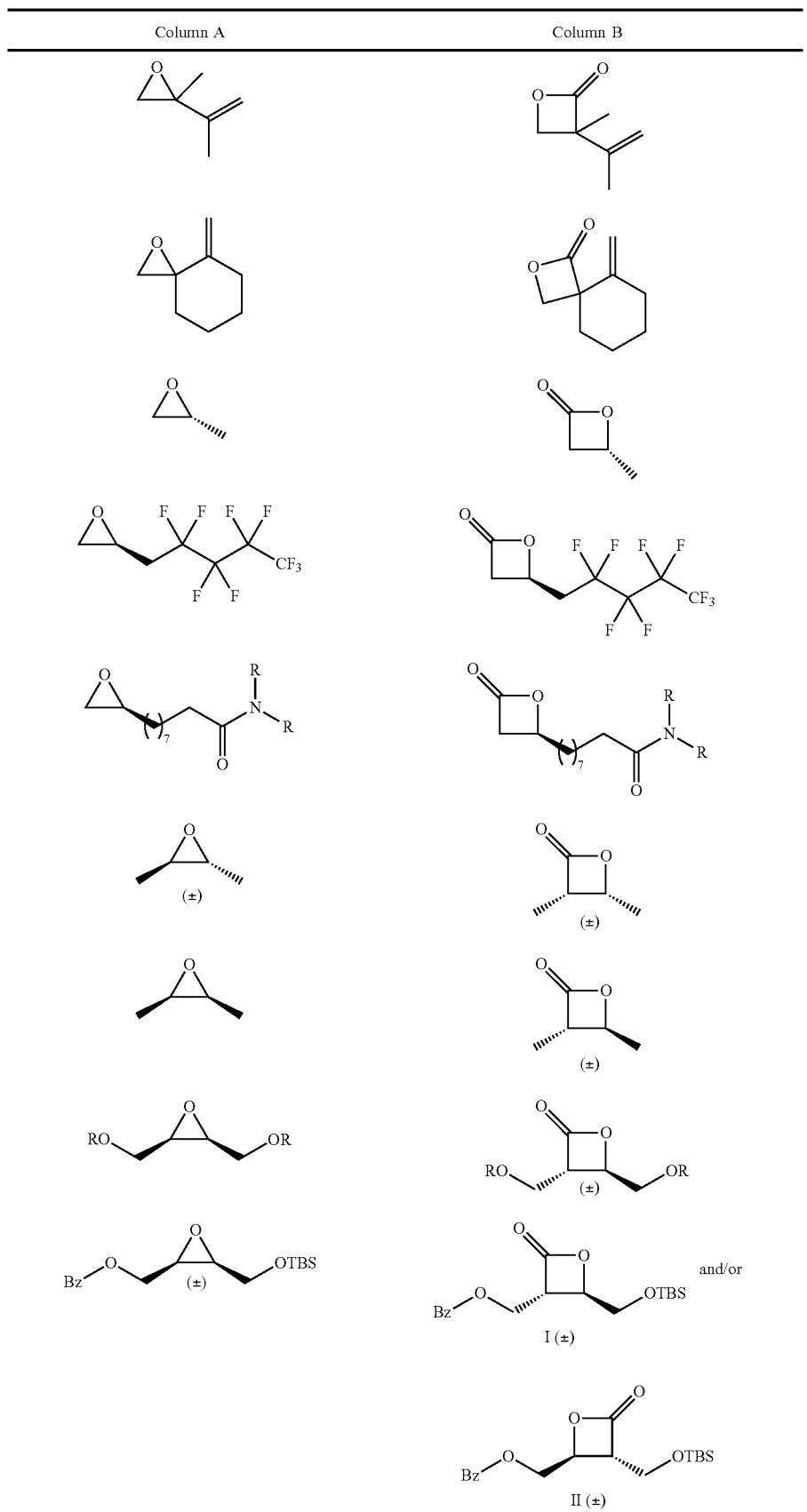

TABLE 1-continued
| Column A | Column B |
|---|---|
| 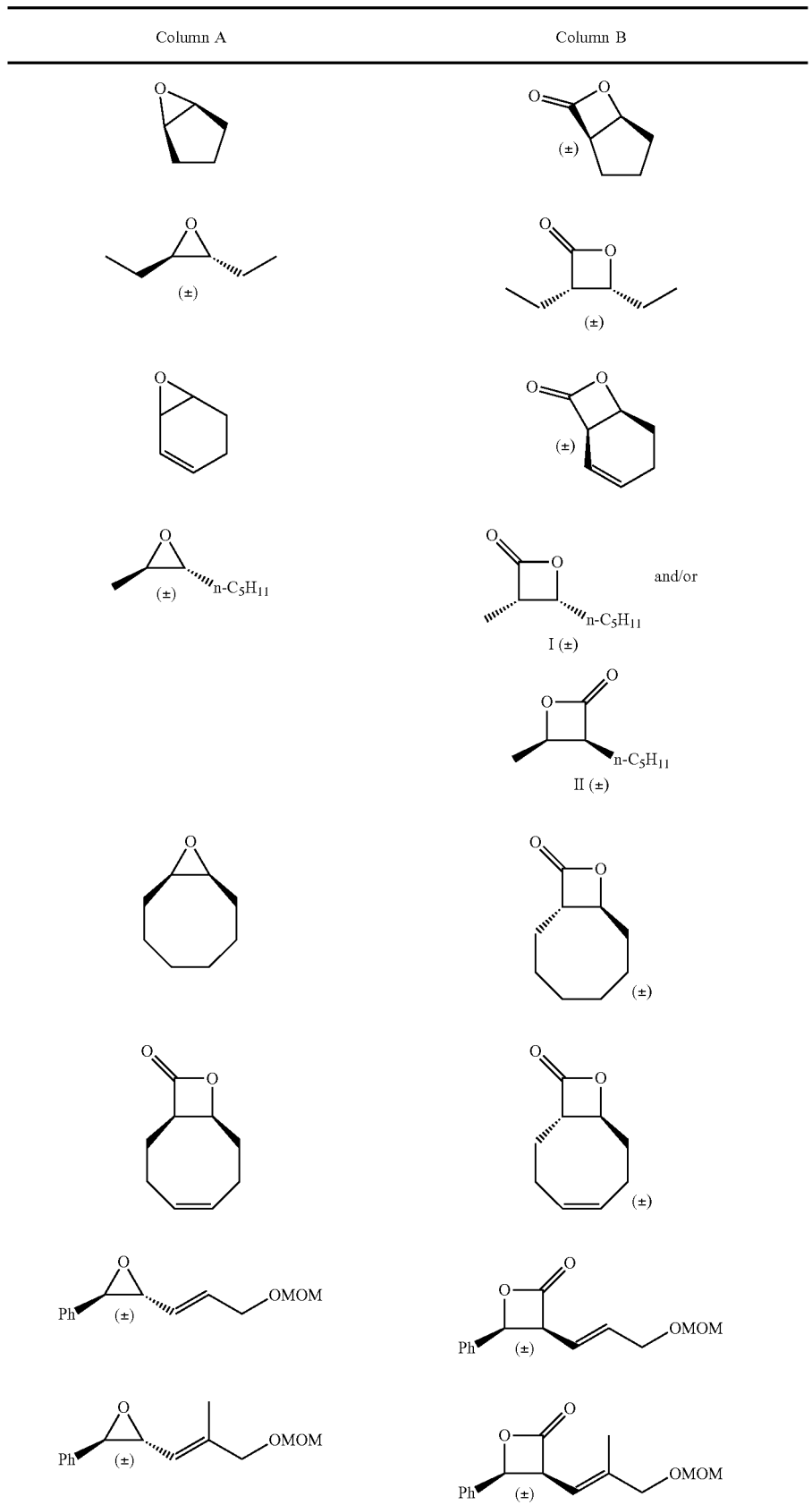 | |

TABLE 1-continued

| Column A | Column B |
|---|---|
| (epoxide of cyclododecane, ±) | (β-lactone of cyclododecane, ±) |
| (epoxide of cyclododecadiene, ±) | (β-lactone with diene) and/or (β-lactone with diene, alternate) |
| n-C$_4$H$_9$–CH=CH–(epoxide)–CH$_2$–CH(OH)–n-C$_5$H$_{11}$ | n-C$_4$H$_9$–CH=CH–(β-lactone)–CH$_2$–CH(OH)–n-C$_5$H$_{11}$ |
| CH$_3$–(CH$_2$)$_7$–(epoxide, ±)–(CH$_2$)$_7$–CO$_2$Me | CH$_3$–(CH$_2$)$_7$–(epoxide)–(CH$_2$)$_7$–CO$_2$Me and/or CH$_3$–(CH$_2$)$_7$–(β-lactone)–(CH$_2$)$_7$–CO$_2$Me |
| diglycidyl ether of glycerol | bis-β-lactone ether of glycerol |
| 1,2:7,8-diepoxyoctane analog | bis-β-lactone analog |
| bis(glycidyl) ether | bis(β-lactone methyl) ether |

Organic Acid Production from Beta-Lactones

In certain preferred embodiments, the processes of the present invention produce an organic acid product directly from a beta-lactone intermediate with a heterogenous catalyst. Such processes produce organic acid products in high yields, by minimizing other by-products that form, such as polylactones and polyorganic acids. Such methods produce at least one organic acid product from at least one beta-lactone reagent in a single step reaction.

The processes for producing an organic acid product from a beta-lactone reagent use a heterogeneous catalyst such as zeolite, metal oxide, supported acid such as phosphoric acid (solid phosphoric acid—SPA), and/or heteropolyacid. In certain preferred embodiments, the at least one heterogeneous catalyst comprises silica-alumina molecular sieves, particularly those modified with phosphate compounds. Catalysts of the type that are specifically suited for this invention include alkaline-earth phosphates, supported phosphate salts, calcium hydroxyapatites, inorganic salts, metal oxides, and zeolites. In preferred embodiments, the at least one heterogeneous catalyst is an alumina-silicate molecular sieve and more preferably a zeolite having Lewis or Brönsted acidity. The zeolites are in hydrogen form or in cation exchanged form. Suitable cations are akali metals such as $Na^+$ or $K+$; alkali-earth cations such as $Ca^{2+}$, $Mg^{2+}$, $Sr^{2+}$, or $Ba^{2+}$; and $Zn^{2+}$, $Cu^+$, and $Cu^{2+}$.

Polymerization of Beta-Lactones

In certain other preferred embodiments, the processes of the present invention include a step for polymerizing the beta-lactone intermediate with a polymerization initiator in the presence of at least one metal cation in at least one reaction vessel to produce a polylactone product 117. In certain preferred embodiments of this invention, the polymerization initiator is an ionic initiator having the general formula of M"X where M" is cationic and X is anionic. The M" is selected from the group consisting of $Li^+$, $Na^+$, $K+$, $Mg2^+$, $Ca^{2+}$, and $Al3^+$. In some embodiments, M" is $Na^+$. In some embodiments, M" is an organic cation. In some embodiments, the organic cation is selected from the group consisting of quaternary ammonium, imidazolium, and bis(triphenylphosphine)iminium. In some embodiments, the quaternary ammonium cation is tetraalkyl ammonium.

The X is a nucleophilic anion such as, but not limited to, compounds comprising at least one carbonxylate group, at least one alkoxide group, at least one phenoxide group, and combination thereof. In some embodiments, the nucleophilic anion is selected from the group consisting of halides, hydroxide, alkoxide, carboxylate, and combination thereof. In some embodiments, the ionic initiator is sodium acrylate. In some embodiments, the ionic initiator is tetrabutylammonium acrylate. The suitable anionic nucleophiles include $R^xO^-$, $R^xC(=O)O^-$, $R^xS^-$, $R^xO(C=O)O^-$, halide (e.g., $Br^-$, $I^-$, $Cl^-$), $R^x(SO_2)O^-$ and $PR^x{}_3O^-$, wherein each $R^x$ is independently selected from hydrogen, optionally substituted aliphatic, optionally substituted heteroaliphatic, optionally substituted aryl and optionally substituted heteroaryl. In certain embodiments where the anionic nucleophile is $R^xC(=O)O^-$, $R^x$ is selected from optionally substituted aliphatic, fluorinated aliphatic, optionally substituted heteroaliphatic, optionally substituted aryl, fluorinated aryl, and optionally substituted heteroaryl. For example, in certain aspects the initiator is $CH_2=CHCO_2^-$, $CH_3CO_2^-$, or $CF_3CO_2^-$.

In certain embodiments, the homogeneous polymerization initiator is a quaternary ammonium salt (for example, tetrabutylammonium (TBA) acrylate, TBA acetate, trimethylphenylammonium acrylate, or trimethylphenylammonium acetate) or a phosphine (for example, tetraphenyl phosphonium acrylate). In some aspects, the catalyst is tetrabutylammonium acrylate, sodium acrylate, potassium acrylate, iron chloride, tetrabutylammonium acetate, trimethylphenylammonium acrylate, trimethylphenylammonium acetate, or tetraphenyl phosphonium acrylate.

The polymerization process further comprises a polymerization initiator including but not limited to amines, polyamines, phosphines amongst others. Further, a variety of polymerization initiators is used in the polymerization process, including but not limited to carbonates of alkali- and alkaline earth metals. In certain aspects, suitable polymerization initiators include carboxylate salts of metal ions or organic cations. In certain aspects, a polymerization initiator is combined with the production stream containing the beta-lactone intermediates. In certain aspects, the molar ratio of the polymerization initiator to the beta-lactone intermediates is about 1:15000. In certain aspects, the molar ratio of polymerization intiator:beta-lactone intermediates is about 1:100, 1:10000, 1:1000, 1:20000 or a range including any two of these ratios.

The polymerization initiator comprises a carboxylate salt, the carboxylate having a structure such that upon initiating polymerization of the beta-lactone intermediate, the polylactone chains produced have an acrylate chain end. In certain aspects, the carboxylate ion on a polymerization initiator is the anionic form of a chain transfer agent used in the polymerization process.

In certain embodiments, steps for polymerizing the beta-lactone intermediate is performed in the presence of a solvent. Suitable solvents for the polymerization with cyclic anhydride monomers include methylene chloride, chloroform, tetrahydrofuran, sulfolane, N-methyl pyrrolidone, diglyme, triglyme, tetraglyme, and dibasic esters.

In some embodiments, suitable catalysts, initiators and solvent for the polymerization of the beta-lactone monomers are found in U.S. Ser. No. 15/197,838 filed Jun. 30, 2016, the contents of which are herein incorporated by reference in its entirety. Other catalysts suitable for the ring-opening polymerization step of the processes disclosed herein are disclosed, for example, in: *Journal of the American Chemical Society* (2002), 124(51), 15239-15248; *Macromolecules*, vol. 24, No. 20, pp. 5732-5733; *Journal of Polymer Science*, Part A-1, vol. 9, No. 10, pp. 2775-2787; *Macromolecules*, vol. 26, No. 20, pp. 5533-5534; *Macromolecules*, vol. 23, No. 13, pp. 3206-3212; Polymer Preprints (1999), 40(1), 508-509; *Macromolecules*, vol. 21, No. 9, pp. 2657-2668; and *Journal of Organometallic Chemistry*, vol. 341, No. 1-3, pp. 83-9; and in U.S. Pat. Nos. 3,678,069; 3,169,945; 6,133,402; 5,648,452; 6,316,590; 6,538,101; and 6,608,170. The entirety of each of which is hereby incorporated herein by reference.

Thermolysis

In preferred embodiments, the processes of the present invention include a step for heating the polylactone product under thermolysis conditions to produce an organic acid product in the at least one reaction vessel defining a thermolysis section. Under thermolysis conditions, the polylactone product can generally be converted to an organic acid according to the following scheme:

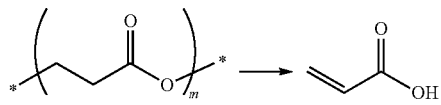

In certain embodiments, the polylactone product may undergo thermolysis continuously (e.g. in a fed batch reactor or other continuous flow reactor format). In certain embodiments, the continuous thermolysis process is linked to a continuous polymerization process to produce the organic acid product at a rate matched to the consumption rate of the at least one reaction vessel.

In certain preferred embodiments of the present invention, the processes include a step for heating the polylactone product under thermolysis conditions to an organic acid product which may favor β-elimination to produce an unsaturated alkenoic acid. Certain exemplary thermolysis reactions are shown below as non-limiting examples:

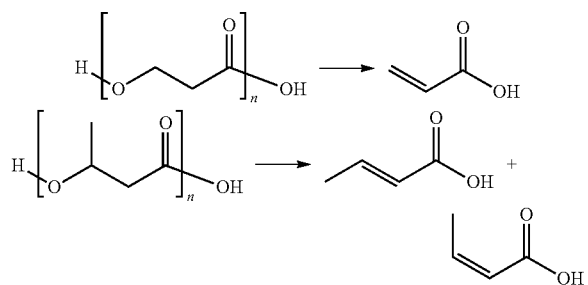

In certain embodiments of the present invention, the epoxide reagent may be a diepoxide, for example, 1,2-butadiene diepoxide. Certain exemplary reactions for producing an organic acid product from a diepoxide are shown below as non-limiting examples In preferred embodiments of the present invention, ammoxidation of the organic acid product with the ammonia reagent proceeds in the presence of a catalyst. In certain preferred embodiments, the catalysts useful for ammoxidation of the one or more organic acid products include metal and/or metal oxides including the group Cr, Al, V, Mn, Fe, Mo, Sn, Bi, and U. In some embodiments, catalysts are supported, such as, on silica in order to decrease the expensive metal content of the catalyst. Certain examples of catalysts useful for ammoxidation of the one or more organic acid products include $Cr_2O_3/Al_2O_3$, $KNaMoP/Al_2O_3$, $NaMo/Al_2O_3$, AsFeO, SbSnO, FeBiPO, BiMoO, $MoO_3$, $MoO_3/SiO_2$, and $NaMo/Al_2O_3$.

In some embodiments, the processes of the present invention include a step for esterification of the organic acid product prior to a step for ammoxidation. The step for esterification includes introducing an alcohol reagent and an acid catalyst to the organic acid product through at least one feed stream inlet of the at least one reaction vessel. In certain embodiments, the step for esterification includes introducing heat the one or more reaction vessels.

Process for Amoxidation

In certain preferred embodiments, an ammoxidation reaction is performed in a fluid bed reactor, a transport line reactor and/or a hybrid reactor. Certain reaction configurations include those described in U.S. Pat. Nos. 3,230,246, and 6,143,915, herein incorporated by reference. In certain embodiments, the one or more reaction vessels defining an ammoxidation section are configured as a fluid bed reactor, for example, introducing solid phase ammoxidation catalyst to the ammoxidation section and passing one or more organic acid products and one or more ammonia reagents in

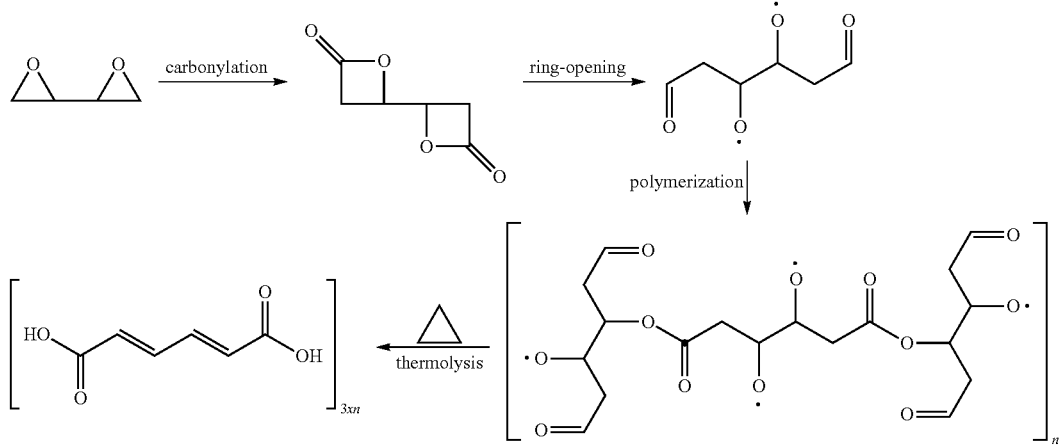

Amoxidation

In certain preferred embodiments, the processes of the present invention include a step for reacting the organic acid product with an ammonia reagent under ammoxidation conditions in at least one reaction vessel to produce an acrylonitrile product 119. Conditions for an ammoxidation reaction are well known in the prior art as evidenced by U.S. Pat. Nos. 5,093,299; 4,863,891; 4,767,878 and 4,503,001; herein incorporated by reference. In the step for ammoxidation of the organic acid product, the organic acid product is reacted with an ammonia reagent. The molar ratio of the ammonia reagent to the organic acid product in the reaction may be in the range of 0.5:1 to 2:1. More preferably, the ratio may be in the range of 0.9:1 to 1.3:1.

liquid phase through the ammoxidation catalyst. In certain embodiments, the one or more reaction vessels defining an ammoxidation section are configured as a transport line reactor, for example, the one or more organic acid products and/or one or more ammonia reagents are circulated through the one or more reaction vessels as a gas at high temperature and high velocity. In certain embodiments, the one or more reaction vessels defining an ammoxidation section are configured as a hybrid reactor, for example, the introducing solid phase ammoxidation catalyst and liquid phase one or more organic acid products to the ammoxidation section and circulating one or more ammonia reagents as a gas at high temperature and high velocity.

In certain embodiments of the present invention, the components of the reactor system for performing the processes of the present invention are in two or more locations which are remote from each other. In some embodiments, one or more reaction vessels defining a polymerization section are in a location remote from one or more reaction vessels defining a thermolysis section.

In certain embodiments, reactor systems for performing the processes of the present invention are characterized in that the location where the one or more polylactone products are produced (i.e. the first location) and the location where at least a portion of the one or more polylactone products undergoes thermolysis to produce one or more organic acids (i.e. the second location) are at least 10 miles apart. In certain embodiments, the first location and the second location are at least 1,000 miles apart. In certain embodiments, the first location and the second location are 5,000 miles apart. In certain embodiments, the first location and the second location are in different countries. In certain embodiments, the first location and the second location are on different continents. Price differences between different locations make it advantageous to form the one or more polylactone products at one location, and to liberate the one or more organic acid products at a different location. The ability to safely store and transport the one or more polylactone products enables the formation of the one or more polylactone products at a first location where the cost of raw materials is less than at a second location, followed by transportation to the second location and subsequent thermolysis to liberate the one or more organic acid products.

Acrylonitrile and Acrylonitrile Derivatives from Beta-Hydroxy Lactones and/or Beta-Hydroxy Amides In another embodiment, methods to produce acrylonitrile compounds and other nitrile compounds from beta-hydroxy amides and/or beta-lactones are provided. In some aspects, provided are methods of producing acrylonitrile compounds and other nitrile compounds from beta-hydroxy amides. For example, with reference to the scheme directly below, a beta-hydroxy amide of formula (2) is combined with a dehydration agent to produce an acrylonitrile compound or other nitrile compounds of formula (3), or isomers thereof.

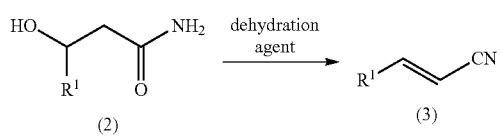

In other aspects, provided are methods of producing acrylonitrile compounds and other nitrile compounds from beta-lactones. For example, with reference to the scheme directly below, a beta-lactone of formula (1) is combined with ammonia (e.g., ammonium hydroxide) to produce the beta-hydroxy amide of formula (2). In some variations, the compound of formula (1) is combined with ammonia in the absence of solvent. In still other variations, the compound of formula (1) is combined with ammonia in water. In yet other variations, the compound of formula (1) is combined with ammonia at room temperature.

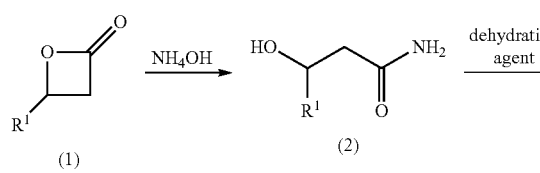

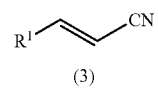

In another example, with reference to the scheme directly below, a beta-lactone of formula (1) is combined with ammonia (e.g., ammonium hydroxide) and a dehydration agent to produce an acrylonitrile compound or other nitrile compounds of formula (3), or isomers thereof. In some variations, the compound of formula (1) is combined with ammonia and a dehydration agent in the absence of solvent. In other variations, the compound of formula (1) is combined with ammonia in water. In still other variations, the compound of formula (1) is combined with ammonia and a dehydration agent at room temperature.

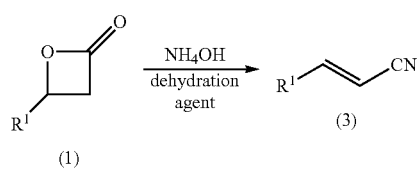

In some variations of the foregoing, the ammonia is aqueous ammonia. In some variations of the foregoing, the ammonia is ammonium hydroxide. The ammonia is obtained from any commercially available sources or produced according to any methods known in the art.

Acrylonitrile Compounds and Acrylonitrile Derivative Compounds

In some embodiments, the acrylonitrile compounds and other nitrile compounds produced according to the methods herein are compounds of formula (3):

wherein $R^1$ is H or alkyl,
or isomers thereof.

In some variations, $R^1$ is H, and the compound of formula (3) is

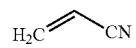

(also known in the art as acrylonitrile).

In other variations, $R^1$ is alkyl. In certain variations, $R^1$ is C1-6 alkyl. In one variation, $R^1$ is methyl or ethyl. When $R^1$ is methyl, the compound of formula (3) is

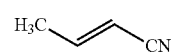

(also known in the art as crotononitrile), or isomers thereof. When $R^1$ is ethyl, the compound of formula (3) is

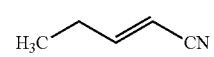

(also known in the art as 2-pentenenitrile), or isomers thereof.

Beta-Hydroxy Amide Intermediate Compounds

In some embodiments, the beta-hydroxy amides that are used to produce acrylonitrile and acrylonitrile derivatives according to the methods herein are compounds of formula (2):

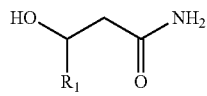
(2)

wherein $R^1$ is H or alkyl,
or isomers thereof.

In some variations, $R^1$ is H, and the compound of formula (2) is

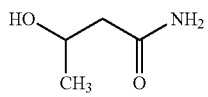

(or 3-hydroxypropanamide).

In other variations, $R^1$ is alkyl. In certain variations, $R^1$ is C1-6 alkyl. In one variation, $R^1$ is methyl or ethyl. When $R^1$ is methyl, the compound of formula (2) is

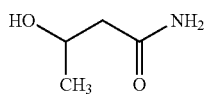

(or 3-hydroxybutanamide). When $R^1$ is ethyl, the compound of formula (2) is

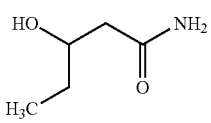

(or 3-hydroxypentanamide).

It should generally be understood that when a compound of formula (2) is used to produce a compound of formula (3), or isomers thereof, $R^1$ of formula (2) is as defined for formula (3).

The beta-hydroxy amides, such as the compounds of formula (2), are obtained from any commercially available sources or produced according to any methods known in the art.

Beta-Hydroxy Lactone Intermediate Compounds

In other embodiments, the beta-lactones that are used to produce acrylonitrile and acrylonitrile derivatives according to the methods herein are compounds of formula (1):

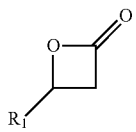

wherein $R^1$ is H or alkyl,
or isomers thereof.

In some variations, $R^1$ is H, and the compound of formula (1) is

(also known in the art as beta-propiolactone).

In other variations, $R^1$ is alkyl. In certain variations, $R^1$ is C1-6 alkyl. In one variation, $R^1$ is methyl or ethyl. When $R^1$ is methyl, the compound of formula (1) is

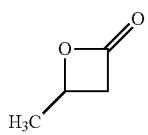

(also known in the art as beta-butyrolactone). When $R^1$ is ethyl, the compound of formula (1) is

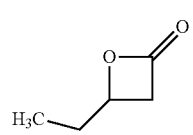

(also known in the art as beta-valerolactone).

It should generally be understood that when a compound of formula (1) is used to produce a compound of formula (2) or a compound of formula (3), or isomers thereof, $R^1$ of formula (1) is as defined for formula (2) or formula (3).

The beta-lactones, such as the compounds of formula (1), are obtained from any commercially available sources or produced according to any methods known in the art. For example, beta-propiolactone is obtained by reacting ethylene oxide and carbon monoxide under suitable conditions.

The beta-lactones, such as the compounds of formula (1), are obtained from renewable feedstock. For example, when beta-propiolactone is produced from ethylene oxide and carbon monoxide, either or both the ethylene oxide and carbon monoxide is obtained from renewable feedstock using methods known in the art. When the beta-lactone, such as the compound of formula (1), is obtained in part or completely from renewable feedstock, the polyamide produced according to the methods described herein from such beta-lactone has a bio-content greater than 0%.

Various techniques are known in the art to determine bio-content of a material. For example, in some variations, bio-content of a material is measured using the ASTM D6866 method, which allows the determination of the bio-content of materials using radiocarbon analysis by accelerator mass spectrometry, liquid scintillation counting, and isotope mass spectrometry. A bio-content result is derived by assigning 100% equal to 107.5 pMC (percent modern carbon) and 0% equal to 0 pMC. For example, a sample measuring 99 pMC gives an equivalent bio-content result of 93%. In one variation, bio-content is determined in accordance with ASTM D6866 revision 12 (i.e. ASTM D6866-12). In another variation, bio-content is determined in accordance with the procedures of Method B of ASTM-D6866-12. Other techniques for assessing the bio-content of materials are described in U.S. Pat. Nos. 3,885,155; 4,427,884; 4,973,841; 5,438,194; and 5,661,299, as well as WO 2009/155086.

Dehydration Agents

In some embodiments, the dehydration agents used in the methods described herein include phosphorous pentoxide, an organophosphorous compound, a carbodiimide compound, a triazine compound, an organosilicon compound, a transition metal complex, or an aluminum complex.

In certain embodiments, the dehydration agents used in the methods described herein further comprise a solid support. Suitable solid supports include, for example, hydrotalcite.

The dehydration agents are obtained from any commercially available sources or prepared according to any methods known in the art. They include the following.

Phosphorous Compounds

In certain embodiments, the dehydration agent used in the methods described herein comprises phosphorous compounds.

In one variation, the dehydration agent comprises phosphorous pentoxide.

In some variations, the dehydration agent comprises an organophosphorous compound. In certain variations, the organophosphorous compound is an organophosphate. In certain variations, the organophosphorous compound is an alkyl halophosphate or a cycloalkyl halophosphate. In one variation, the alkyl halophosphate is alkyl dihalophosphate or dialkyl halophosphate. In another variation, the cycloalkyl halophosphate is cycloalkyl dihalophosphate, or dicycloalkyl halophosphate. In some variations of the foregoing organophosphorous compounds, the alkyl is a C1-C10 alkyl. In other variations of the foregoing organophosphorous compounds, the cycloalkyl is a C3-C10 cycloalkyl.

In yet other variations of the foregoing organophosphorous compounds, the halophosphate is chlorophosphate. In yet other variations of the foregoing organophosphorous compounds, the halophosphate is fluorophosphate. Suitable organophosphorous compounds used in the methods described herein include, for example, ethyl dichlorophosphate, diethyl chlorophosphate, methyl dichlorophosphate, dimethyl chlorophosphate, ethyl difluorophosphate, diethyl fluorophosphate, methyl difluorophosphate, or dimethyl fluorophosphate, or any combination thereof.

Carbodiimide Compounds

In certain embodiments, the dehydration agent comprises a carbodiimide compound.

In some variations, the carbodiimide compound is $R^4$—N=C=N—$R^5$, wherein each $R^4$ and $R^5$ is independently alkyl or cycloalkyl. In certain variations of the foregoing, $R^4$ and $R^5$ are different. In other variations of the foregoing, $R^4$ and $R^5$ are the same. In other variations, each $R^4$ and $R^5$ is independently cycloalkyl.

In certain variations, each $R^4$ and $R^5$ is independently alkyl. In certain variations, each $R^4$ and $R^5$ is independently is independently C1-6 alkyl. In one variation, each $R^4$ and $R^5$ is independently is methyl, ethyl or propyl. In another variation, $R^4$ and $R^5$ are both methyl, ethyl or propyl. In another variation, $R^4$ and $R^5$ are both cyclohexyl. In yet other variations, $R^4$ is alkyl, and $R^5$ is cycloalkyl.

Suitable carbodiimide compounds used in the methods described herein include, for example,

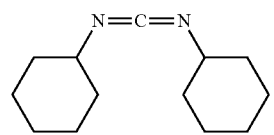 [SMILES: C(=NC1CCCCC1)=NC1CCCCC1]

(also known in the art as N,N'-dicyclohexylcarbodiimide), in which $R^4$ and $R^5$ are both cyclohexyl.

Triazine Compounds

In certain embodiments, the dehydration agent comprises a triazine compound. In one variation, the triazine compound is 1,3,5-triazine, which has the following structure:

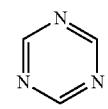

The triazine compounds described herein are optionally substituted with one or more substituents. In some variations, the triazine compound is substituted with 1, 2 or 3 substituents. In certain variations, the substituents are halo groups. For example, in certain variations, the triazine compound is a halo-substituted triazine compound. In certain variations, the triazine compound is 1,3,5-triazine substituted with 1, 2, or 3 halo groups. In one variation, the triazine compound is a halo-substituted 1,3,5-triazine.

Suitable triazine compounds used in the methods described herein may include, for example,

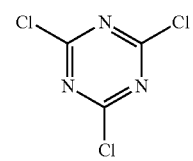

(also known in the art as cyanuric chloride).

Organosilicon Compounds

In certain embodiments, the dehydration agent comprises an organosilicon compound. In some variations, the organosilicon compound is a silazane. The silazane is unsubstituted or substituted. In one variation, the silazane is substituted with aryl, halo, alkyl, alkoxy or amino groups.

In certain embodiments, the organosilicon compound is

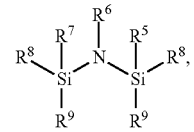

wherein each $R^6$, $R^7$, $R^8$ and $R^9$ (at each occurrence) is independently H, alkyl, cycloalkyl, heteroalkyl, heterocycloalkyl, aryl, heteroaryl, halo, amino, or alkoxy.

In other variations, the organosilicon compound is a silane. The silane is unsubstituted (e.g. a hydrosilane) or substituted. In some variations, the silane is substituted with 1, 2, 3 or 4 substituents. In one variation, the silane is substituted with aryl, halo, alkyl, alkoxy or amino groups.

In certain embodiments, the organosilicon compound is

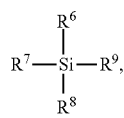

wherein each of $R^6$, $R^7$, $R^8$ and $R^9$ is independently H, alkyl, cycloalkyl, heteroalkyl, heterocycloalkyl, aryl, heteroaryl, halo, amino, or alkoxy.

In one embodiment, the organosilicon compound is an arylsilane. In some variations, the arylsilane comprises 1, 2 or 3 aryl groups. In variations of the foregoing, the aryl group is phenyl. Suitable arylsilanes include, for example, diphenylsilane and phenylsilane. In one variation, the organosilicon compound is $Ph_2SiH_2$. In another variation, the organosilicon compound is $PhSiH_3$. In other embodiments, the organosilicon compound is a halosilane, an alkoxysilane, or an aminosilane. In one embodiment, the organosilicon compound is a halosilane. In some variations, the halosilane comprises 1, 2 or 3 halo groups. In certain variations, the halosilane may be further substituted with one or more substituents (other than halo). In one variation, the halosilane is further substituted with 1, 2 or 3 substituents (other than halo). In variations of the foregoing, the substituents of the halosilane are independently alkyl or aryl. In one variation of the foregoing, the alkyl substituent of the halosilane is C1-6 alkyl. In another variation, the substituents of the halosilane are independently methyl or phenyl. Suitable halosilanes include, for example, dialkyldihalosilane, aryltrihalosilane, arylalkyldihalosilane, or aryltrihalosilane. In certain variations, the halosilane is a chlorosilane. Suitable chlorosilanes include, for example, dimethyldichlorosilane, phenyltrichlorosilane, or phenylmethyldichlorosilane.

In another embodiment, the organosilicon compound is an alkoxysilane. In certain variations, the alkoxysilane comprises an alkylsilicate. In one variation, the alkoxysilane comprises a C1-6 alkylsilicate. Suitable alkylsilicates include, for example, n-butylsilicate. In other variations, the alkoxysilane comprises 1, 2 or 3 alkoxy groups. In certain variations of the foregoing, the alkoxysilane is further substituted with 1, 2 or 3 substituents (other than alkoxy). In one variation, the substituents of the alkoxysilane are independently alkyl or aryl. In one variation of the foregoing, the alkyl substituent of the alkoxysilane is C1-6 alkyl. In another variation, the substituents of the alkoxysilane are independently methyl or phenyl. Suitable alkoxysilanes include, for example, dimethoxy(methyl)phenylsilane.

In yet another embodiment, the organosilicon compound is an aminosilane. In certain variations, the aminosilane is an alkylaminosilane. In certain variations of the foregoing, the aminosilane is further substituted with 1, 2 or 3 substituents (other than an amino group, including, for example, an alkylamino group). In one variation, the substituents of the aminosilane are alkoxy groups. In one variation of the foregoing, the alkoxy substituent of the aminosilane is C1-6 alkoxy. In another variation, the substituents of the aminosilane are independently methoxy or ethoxy. Suitable aminosilanes may include, for example, (3-aminopropyl)triethoxysilane.

In other embodiments, the organosilicon compound is bis(trialkylsilyl)amine. In one variation, the organosilicon compound is bis(trimethylsilyl)amine.

In some variations of the foregoing, the silanes described herein are used in combination with an alkylammonium halide as the dehydration agent. In one variation, the alkylammonium halide is tetrabutylammonium halide, such as tetrabutylammonium chloride or tetrabutylammonium fluoride. In certain variations, the organosilicon compound and the alkylammonium halide are provided as a mixture (e.g. in a solvent) or separately combined.

Transition Metal Complexes

In certain embodiments, the dehydration agent comprises a transition metal complex. In some variations, the transition metal complex comprises at least one halide or oxide ligand. The halide or oxide ligand may be associated or complexed with the transition metal.

In certain variations of the foregoing, the transition metal complex is provided in a solvent. In other variations, the transition metal complex is provided in water or acetonitrile, or a mixture thereof.

In one embodiment, the transition metal complex is a metal halide. In some variations, the metal halide comprises a Group 10 metal or a Group 12 metal. In certain variations, the metal halide comprises palladium or zinc. In certain variations, the metal halide comprises chloro. Suitable metal halides include, for example, palladium chloride or zinc chloride.

In some variations of the foregoing, the metal halide is provided in a solvent. In one variation, the metal halide is provided in water, acetonitrile or a mixture thereof. For example, the transition metal complex used in the methods described herein is palladium chloride or zinc chloride provided in water, acetonitrile or a mixture thereof.

In another embodiment, the transition metal complex comprises a Group 5 metal. In some variations, the transition metal complex comprises a vanadium oxide. In one variation, the vanadium oxide is monomeric vanadium oxide. In a certain variation, the dehydration agent comprises vanadium oxide and hydrotalcite. In one variation, the dehydration agent comprises monomeric vanadium oxide and hydrotalcite. The vanadium oxide (including, for example, monomeric vanadium oxide) is incorporated on the surface of hydrotalcite.

Aluminum Complexes

In certain embodiments, the dehydration agent comprises an aluminum complex. In some variations, the aluminum complex comprises an aluminum halide. In certain variations, the aluminum complex is complexed with water, acetonitrile, or an alkali metal salt, or a mixture thereof. In some variations, the alkali metal salt is a sodium salt or a potassium salt. In some variations, the alkali metal salt is an alkali metal halide salt. In some variations, the alkali metal halide salt is an alkali metal iodide salt. In some variations, the alkali metal halide salt is sodium iodide or potassium iodide. In some variations, the aluminum complex is $AlCl_3.H_2O/KIH_2)/CH_3CN$. In some variations, the aluminum complex is $AlCl_3.NaI$.

Combinations of Dehydration Agents

It should be understood that, in some variations, the term "dehydration agent" includes a combination of agents. In some variations of the methods described herein, a combination of the dehydration agents described herein is used.

In some embodiments, the dehydration agent comprises a combination of an organosilicon compound and a transition metal complex. In certain variations of the foregoing combination, the organosilicon compound is N-methyl-N-(trimethylsilyl)trifluoroacetamide. In some variations of the foregoing combination, the transition metal complex is a metal triflate or a metal halide. In one variation, the metal triflate is zinc triflate. In another variation, the metal halide is copper chloride.

In other embodiments, the dehydration agent comprises a combination of a silane and a transition metal complex. In certain variations of the foregoing combination, the transition metal complex is an iron complex. In one variation, the dehydration agent comprises a combination of a silane and an iron complex.

In other variations of the combination of a silane and a transition metal complex, the transition metal complex is metal carbonate. In certain variations, the metal carbonate comprises iron. In certain variations, the metal carbonate is an iron carbonate. Suitable metal carbonates include, for example, $Fe_2(CO)_9$. In some variations of the foregoing combination, the organosilicon compound is an alkoxyalkylsilane. In certain variations, the alkoxyalkylsilane is diethoxymethylsilane. In one variation, the dehydration agent comprises a combination of iron carbonate and an alkoxyalkylsilane.

Exemplary combinations of dehydration agents used in the methods described herein include zinc triflate and N-methyl-N-(trimethylsilyl)trifluoroacetamide; copper chloride and N-methyl-N-(trimethylsilyl)trifluoroacetamide; an iron complex and a silane; and iron carbonate and diethoxymethylsilane.

In still another embodiment, provided is a composition comprising:
a compound of formula (2)

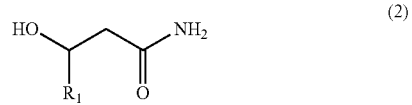

(2)

wherein $R^1$ is H or alkyl; and
a dehydration agent comprising phosphorous pentoxide, an organophosphorous compound, a carbodiimide compound, a triazine compound, an organosilicon compound, a transition metal complex, or an aluminum complex, or any combination thereof.

In certain aspects, the composition further comprises a compound of formula (3):

(3)

wherein $R^1$ is as defined above for formula (2),
or isomers thereof.

In some variations of the foregoing, the composition further comprises
a compound of formula (1):

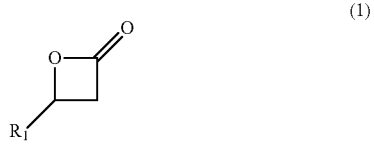

(1)

wherein $R^1$ is as defined above for formula (2); and
ammonia.

In other aspects, provided is a composition comprising a compound of formula (1) as defined above, ammonia and a dehydration agent comprising phosphorous pentoxide, an organophosphorous compound, a carbodiimide compound, a triazine compound, an organosilicon compound, a transition metal complex, or an aluminum complex, or any combination thereof.

In some variations of the foregoing, the composition further comprises a compound of formula (3) as defined above, or isomers thereof.

In some variations, any of the compounds of formula (1), (2) and/or (3), and the dehydration agent (including combination of dehydration agents) described herein for the methods are present in the foregoing compositions.

Uses of Acrylonitrile and Acrylonitrile Derivatives

Acrylonitrile and acrylonitrile derivatives produced according to the methods described herein are, in some variations, used as a monomer for the industrial production of polymers.

For example, acrylonitrile produced according to the methods described herein are used in the production of polyacrylonitrile (PAN). In some aspects, provided is a method of producing polyacrylonitrile, comprising: producing acrylonitrile according to any of the methods described herein; and polymerizing the acrylonitrile under suitable conditions known to those skilled in the art to produce polyacrylonitrile, i.e. free radical polymerization of acrylonitrile. For example, polyacrylonitrile fiber is generally produced by wet or dry-jet-wet spinning of spinning dope in which an acrylonitrile monomer or copolymer is dissolved in an organic or inorganic solvent for transformation of the spinning dope into fiber followed by stretching, washing, and drying for densification of the thus formed fiber.

In other aspects, acrylonitrile produced according to the methods described herein are used in the production of acrylic acid.

Carbon Fiber Production

Polyacrylonitrile produced by the methods described herein is used as a precursor for the industrial production of carbon fibers as follows. Acrylonitrile is produced from at least one of an epoxide or carbon monoxide starting material that is derived from a bio-based and/or renewable source. The acrylonitrile is polymerized to produce a polyacrylonitrile precursor. The polyacrylonitrile precursor is thermally stabilized to afford thermally stabilized carbon fibers. The thermally stabilized carbon fibers are carbonized to produce the carbon fiber material.

Generally, the industrial production of carbon fibers undergoes a stabilization step of heat-treating precursor fibers made of polyacrylonitrile in air with a temperature of 200-3000° C. and a carbonization step of heat-treating the stabilized fibers obtained in the stabilization step in an inert atmosphere with a temperature of 300-3,000° C. A variety of methods and materials using this general concept for making carbon fibers and therefore carbon-carbon composites therefrom through a polyacrylonitrile precursor are described in numerous patents including, for example, S. J. Park, Carbon Fibers—Chapter 2 (Precursors and Manufacturing of Carbon Fibers, Springer Series in Materials Science 210, 2015; U.S. Pat. Nos. 3,914,395; 4,069,297; 4,178,413; 5,061,414; 4,554,024; 5,686,027; 6,638,883; 8,137,810; 8,845,938; 9,212,236; and 9,683,314, all of which are incorporated herein by reference.

According to another embodiment of the invention, a thermal stabilization process is employed. A thermal stabilization process as described herein is critical to obtaining high-quality carbon fibers and can take up to several hours, depending on the temperature, precursor diameter and precursor fiber characteristics. Proper conditions such as heating rate, time, and temperature of heating are established for the optimum stabilization of each precursor. Preferably, the PAN-based polymer precursor is stabilized by controlled low-temperature heating over the range 200-300° C. in air to convert the precursor to a form, which can further be heat-treated without either the melting or fusion of the fibers. In this process, the linear molecules of PAN-based polymer precursor are first converted into cyclic structures.

The carbonization and graphitization of thermally stabilized fibers are preferably carried out in an inert atmosphere containing gases such as nitrogen or argon. More preferably, argon is used as the inert gas despite being eight times more expensive than nitrogen, because argon provides improved strength to the carbon fiber owing to the higher density of the same. The temperature of carbonization is usually determined by the type of application of the resulting carbon fibers. For high-strength applications, the carbonization temperature over the range 1,500-1,600° C. is preferred because at temperatures above 1,600° C., a decrease in the tensile strength occurs. On the other hand, an additional heat treatment above 1,600-1,800° C. and up to 3,000° C., i.e., graphitization process, is required to obtain a high modulus in the carbon fibers. Nitrogen cannot be used at temperatures above approximately 2,000° C. owing to its reaction with carbon to form cyanogen. The heating rate and retention time during carbonization are different depending on the type of the precursor and stabilization conditions.

With respect to graphite structure, dehydrogenation joins the ladder molecules to form graphite-like ribbons; however, denitrogenation makes the ribbons to form sheet-like structures. On the other hand, the high carbonization temperature causes the ordered structure to grow in both thickness and area, thereby increasing the crystalline orientation in the fiber direction, and reduces the interlayer spacing and void content. In addition, the graphite structures can further grow at higher temperatures resulting from the elimination of nitrogen.

Optionally, the surface treatment of carbon fibers is performed to improve the mechanical properties of the composite through alteration of the fiber surface. For example, the most often used surface treatment method for carbon fibers is a liquid and gaseous oxidation treatment. The liquid oxidation treatment is well known and can double the composite shear strengths with slight reductions (4-6%) in fiber tensile strengths. Preferably, the liquid oxidation treatment method is an anodic oxidation treatment, which is inexpensive, fast and efficient. In this method, Faraday's Law applies and the duration of the surface treatment is related to the line speed. In addition, the current density as a standard variable is used to control the treatment level per unit length of carbon fiber during the surface treatment, usually expressed as C/m. The electrically conductive carbon fibers form the anode during the electrolysis of an acid or a salt solution such as, for example, nitric acid, sulfuric acid, ammonium sulfate, and ammonium bicarbonate. Preferably, ammonium sulfate is used as the salt in the surface treatment processes of carbon fibers. Carbonyl containing groups such as COOH form on the smooth fiber surface. The carbonyl groups improve the cohesion between the fiber and resin used in the final composite. After surface treatment, the excess electrolyte is preferably removed using warm water wash treatment. The carbon fibers are then optionally passed onto a next process through one or more water baths constantly flowing with water.

Carbon fibers can then optionally be pre-dried for sizing treatment, and the sizing materials are selected such that they protect the physical characteristics of carbon fibers. These sizing materials need to provide consistent handling and not build up residue on the processing equipment. The sizing materials also need to be compatible with a matrix resin. This includes solubility in and/or reactivity with the formulated resin. This allows the resin to penetrate the fiber bundle and interact with the fiber surface. Preferably, epoxy resins or epoxy formulations are used as sizing materials. The sizing materials should not change either the chemical or physical characteristics of the carbon fibers during storage. Some sizing materials are water soluble and washable after either weaving or braiding. The fiber sizing, process to apply sizing, and sizing content are critical factors in the carbon fiber specification. The type of size material and particle size of the aqueous dispersion is controlled to establish good properties in the carbon fibers after sizing. From these viewpoints, the types of emulsifier and resin and their respective concentrations are key to improving the characteristics of the carbon fibers. The control of wetting in the sizing bath is needed to control the level of size on the carbon fibers. All the steps pertaining to the application of the sizing to the carbon fiber and drying must also be consistent. Many sizing materials such as epoxy resins are not soluble in water and must be applied as a dispersion of emulsion in water. This can result in the sizing being uniformly distributed on the surface of the fibers. Alternately, the sizing materials can exist as either droplets on the fiber surface or by sticking together a number of individual fibers. The particle size of the emulsion in the sizing bath is controlled to provide a dependable product. After sizing, the dried carbon fibers are optionally collected using, for example, winders.

As stated above, the polyacrylonitrile fiber produced by the methods described herein are used as a precursor for the industrial production of carbon fibers. For example, a specific embodiment includes a method of producing a carbon fiber material, the method comprising: a) affording acrylonitrile from at least one of an epoxide or carbon monoxide starting material that is derived from a bio-based and/or renewable source; b) polymerizing the acrylonitrile to produce a polyacrylonitrile precursor; c) thermally stabilizing the polyacrylonitrile precursor to afford thermally stabilized carbon fibers; and d) carbonizing the thermally stabilized carbon fibers to produce the carbon fiber material. The acrylonitrile is afforded, for example, as described herein, for example by a process comprising: a) introducing the at least one of bio-based and/or renewable sourced epoxide and carbon monoxide starting materials to at least one reaction vessel through at least one feed stream inlet; b) contacting the at least one of bio-based and/or renewable sourced epoxide and carbon monoxide starting materials with a carbonylation catalyst in the at least one reaction vessel to produce a beta-lactone intermediate; c) contacting the beta-lactone intermediate with a heterogenous catalyst to produce an organic acid intermediate; and d) reacting the organic acid product with an ammonia reagent under ammoxidation conditions in the at least one reaction vessel to produce the acrylonitrile product.

The acrylonitrile can also have a formula (3):

(3)

wherein R¹ is H or alkyl, or isomers thereof, the acrylonitrile produced by a method comprising: a) combining a compound of formula (2) with a dehydration agent to produce the compound of formula (3), or isomers thereof, wherein the compound of formula (2) is

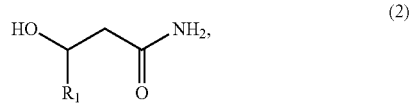

(2)

wherein R¹ is as defined above for formula (3), and the dehydration agent comprises phosphorous pentoxide, an organophosphorous compound, a carbodiimide compound, a triazine compound, an organosilicon compound, a transition metal complex, or an aluminum complex, or any combination thereof.

Carbon Black

While the methods provided herein keep production of carbon black to a minimum, in contrast to prior art methods affording acrylonitrile or polyacrylonitrile, carbon black is produced as a byproduct. The carbon black byproduct is produced during the processing of the polyacrylonitrile polymers during the production of carbon fiber. Carbon black byproduct can be mechanically removed from the polyacrylonitrile polymer fiber precursor by performing at least one of heating the precursor polymer fiber, stretching the precursor polymer and/or polishing the same. The carbon black can be collected and combined with carbon fiber, for example, to produce a bio-based tire.

It is also to be understood that when the carbon fibers or carbon black is obtained in part or completely from renewable feedstock, the polyacrylonitrile or polyacrylonitrile derivative produced according to the methods described herein from the molecules obtained from the renewable source has a bio-content greater than 0%. Thus, the carbon fiber and carbon black produced by the methods disclosed herein also have a bio-content greater that 0%. As such, the carbon fibers provided by the methods of the instant invention overcome the shortcomings of the prior art methods. Conventional polyacrylonitriles made from acrylonitrile produced by prior art methods are more resistant to wet spinning, produce non-uniform surfaces, and therefore produce more carbon black when carbonized. These deficiencies of the prior art methods are reduced or avoided altogether with the methods provided herein.

For example, biological material may be gasified to produce biobased carbon monoxide. Biobased ethylene oxide may be obtained from ethanol derived from corn or other starchy feedstocks. Biobased ammonia can be obtained from many sources. With such biobased starting materials, a green route may be pursued to obtain these products.

The embodiments described herein are not intended to be limited to the aspects shown but are to be accorded the widest scope consistent with the principles and features disclosed herein.

What is claimed is:

1. A method of producing a carbon fiber material, the method comprising:
   a. forming acrylonitrile from at least one of an epoxide or carbon monoxide starting material that is derived from a bio-based and/or renewable source;
   b. polymerizing the acrylonitrile to produce a polyacrylonitrile precursor;
   c. thermally stabilizing the polyacrylonitrile precursor to afford thermally stabilized carbon fibers; and
   d. carbonizing the thermally stabilized carbon fibers to produce the carbon fiber material.

2. The method from claim 1, wherein the acrylonitrile is produced by a process comprising:
   a. introducing the at least one of bio-based and/or renewable sourced epoxide and carbon monoxide starting materials to at least one reaction vessel through at least one feed stream inlet;
   b. contacting the at least one of bio-based and/or renewable sourced epoxide and carbon monoxide starting materials with a carbonylation catalyst in the at least one reaction vessel to produce a beta-lactone intermediate;
   c. contacting the beta-lactone intermediate with a heterogenous catalyst to produce an organic acid product; and
   d. reacting the organic acid product with an ammonia reagent under ammoxidation conditions in the at least one reaction vessel to produce the acrylonitrile product.

3. The method from claim 1, wherein the polyacrylonitrile precursor comprises polyacrylonitrile fibers produced by wet or dry-jet-wet spinning of an acrylonitrile monomer or copolymer.

4. The method from claim 1, wherein the polyacrylonitrile precursor is thermally stabilized by controlled low-temperature heating over the range 200-300° C. in air.

5. The method from claim 1, wherein the carbon fiber material is surface treated to afford a carbon fiber composite.

6. The method from claim 1, wherein the thermally stabilized carbon fibers are carbonized at a carbonization temperature over a range of 1,500-1,600° C.

7. The method from claim 6, wherein the thermally stabilized carbon fibers are additionally heat-treated above 1,600° C. and up to 3,000° C. to afford a graphitized carbon fiber material.

8. The process from claim 3, wherein the polyacrylonitrile precursor further comprises carbon black byproduct, the carbon black byproduct mechanically removed from the polyacrylonitrile precursor by performing at least one of heating, stretching and/or polishing the polyacrylonitrile precursor.

9. The process from claim 2, wherein the process further comprises the steps: polymerizing the beta-lactone intermediate with a polymerization initiator in the at least one reaction vessel to produce a polylactone product; and heating the polylactone product under thermolysis conditions in the at least one reaction vessel to produce the organic acid product.

10. The method from claim 1, wherein the acrylonitrile is produced by a process comprising:
   a. introducing the at least one of bio-based and/or renewable sourced epoxide and carbon monoxide starting materials to at least one reaction vessel through at least one feed stream inlet;
   b. contacting the at least one of bio-based and/or renewable sourced epoxide and carbon monoxide starting materials with a carbonylation catalyst in the at least one reaction vessel to produce a beta-lactone intermediate;
   c. contacting the beta-lactone intermediate with a heterogenous catalyst to produce an organic acid product;
   d. reacting the organic acid product with an alcohol reagent in the at least one reaction vessel to produce an ester product; and e. reacting the ester product with an ammonia reagent under ammoxidation conditions in the at least one reaction vessel to produce the acrylonitrile product.

11. The method of claim 1, wherein the acrylonitrile has a formula (3):

(3)

wherein $R^1$ is H or alkyl, or isomers thereof, the acrylonitrile produced by a method comprising:
combining a compound of formula (2) with a dehydration agent to produce the compound of formula (3), or isomers thereof, wherein:
the compound of formula (2) is

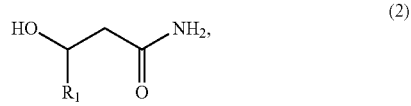

(2)

wherein $R^1$ is as defined above for formula (3), and
the dehydration agent comprises phosphorous pentoxide, an organophosphorous compound, a carbodiimide compound, a triazine compound, an organosilicon compound, a transition metal complex, or an aluminum complex, or any combination thereof.

12. The method of claim 11, further comprising combining a compound of formula (1) with ammonia to produce the compound of formula (2), wherein:
the compound of formula (1) is

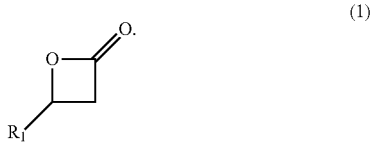

(1)

13. The method of claim 12, wherein the ammonia is ammonium hydroxide or aqueous ammonia.

14. The method of claim 11, wherein the dehydration agent comprises an organophosphorous compound selected from the group consisting of ethyl dichlorophosphate, diethyl chlorophosphate, methyl dichlorophosphate, dimethyl chlorophosphate, ethyl difluorophosphate, diethyl fluorophosphate, methyl difluorophosphate, and dimethyl fluorophosphate, or any combination thereof.

15. The method of claim 11, wherein the dehydration agent comprises a carbodiimide compound having a formula $R^4$—N═C═N—$R^5$, wherein each $R^4$ and $R^5$ is independently alkyl or cycloalkyl.

16. The method of claim 15, wherein the carbodiimide compound is N, N'-dicyclohexylcarbodiimide.

17. The method of claim 11, wherein the dehydration agent comprises a triazine compound that is a halo-substituted triazine compound.

18. The method of claim 17, wherein the triazine compound is 1,3,5-triazine or cyanuric chloride.

19. The method of claim 11, wherein the dehydration agent comprises an organosilicon compound that is a silazane or a silane.

20. The method of claim 19, wherein the silane is bis(trimethylsilyl)amine.

21. The method of claim 11, wherein the dehydration agent comprises an organosilicon compound that is a hydrosilane, and an alkylammonium halide.

22. The method of claim 21, wherein the alkylammonium halide is tetrabutylammonium fluoride.

23. The method of claim 11, wherein the dehydration agent comprises a transition metal complex further comprising at least one halide or oxide ligand.

24. The method of claim 23, wherein the transition metal complex comprises a compound selected from the group consisting of palladium chloride, zinc chloride and vanadium oxide.

25. The method of claim 11, wherein the dehydration agent comprises an organosilicon compound and a transition metal complex.

26. The method of claim 11, wherein the dehydration agent comprises: (i) zinc triflate and N-methyl-N-(trimethylsilyl)trifluoroacetamide; or (ii) copper chloride and N-methyl-N-(trimethylsilyl)trifluoroacetamide; or (iii) an iron complex and a silane; or (iv) iron carbonate and diethoxymethylsilane.

27. The method of claim 11, wherein the dehydration agent comprises an aluminum complex that comprises $AlCl_3 \cdot H_2O/KI/H_2)/CH_3CN$.

28. The process from claim 9, wherein the polymerization initiator comprises a compound having the general formula of M"X where M" is cationic and X is anionic.

29. The process from claim 9, wherein the polymerization initiator comprises a carboxylate salt.

30. The process from claim 9, wherein the polylactone product undergoes thermolysis continuously.

* * * * *